US008236862B2

(12) United States Patent
Chen et al.

(10) Patent No.: US 8,236,862 B2
(45) Date of Patent: Aug. 7, 2012

(54) THERAPEUTIC COMPOSITIONS COMPRISING MONOTERPENES

(75) Inventors: Thomas C. Chen, Los Angeles, CA (US); Clovis O. da Fonseca, Rio de Janeiro (BR); Thereza Quirico dos Santos, Niterói (BR); Gilberto Schwartsmann, Porto Alegre (BR)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/700,614

(22) Filed: Feb. 4, 2010

(65) Prior Publication Data
US 2010/0226913 A1 Sep. 9, 2010

Related U.S. Application Data

(60) Provisional application No. 61/150,714, filed on Feb. 6, 2009.

(51) Int. Cl.
*A61K 31/045* (2006.01)
(52) U.S. Cl. .......................... 514/729; 514/724; 554/229
(58) Field of Classification Search .......................... None
See application file for complete search history.

(56) References Cited

U.S. PATENT DOCUMENTS

| | | | |
|---|---|---|---|
| 3,632,782 A | 1/1972 | Alburn et al. |
| 3,957,856 A | 5/1976 | Ansari et al. |
| 4,107,288 A | 8/1978 | Oppenheim et al. |
| 4,353,365 A | 10/1982 | Hallworth et al. |
| 4,524,769 A | 6/1985 | Wetterlin |
| RE32,241 E | 9/1986 | Saxer |
| 4,666,456 A | 5/1987 | Thijssen et al. |
| 4,738,851 A | 4/1988 | Schoenwald et al. |
| 4,882,150 A | 11/1989 | Kaufman |
| 4,921,475 A | 5/1990 | Sibalis |
| 5,008,110 A | 4/1991 | Benecke et al. |
| 5,035,237 A | 7/1991 | Newell et al. |
| 5,077,033 A | 12/1991 | Viegas et al. |
| 5,087,240 A | 2/1992 | Sibalis |
| 5,088,977 A | 2/1992 | Sibalis |
| 5,127,921 A | 7/1992 | Griffiths |
| 5,145,684 A | 9/1992 | Liversidge et al. |
| 5,163,899 A | 11/1992 | Sibalis |
| 5,164,189 A | 11/1992 | Farhadieh et al. |
| 5,225,183 A | 7/1993 | Purewal et al. |
| 5,239,993 A | 8/1993 | Evans |
| 5,254,346 A | 10/1993 | Tucker et al. |
| 5,290,561 A | 3/1994 | Farhadieh et al. |
| 5,332,213 A | 7/1994 | Klose |
| 5,336,168 A | 8/1994 | Sibalis |
| 5,352,456 A | 10/1994 | Fallon et al. |
| 5,403,841 A | 4/1995 | Lang et al. |
| 5,407,713 A | 4/1995 | Wilfong et al. |
| 5,414,019 A | 5/1995 | Gould et al. |
| 5,415,162 A | 5/1995 | Casper et al. |
| 5,521,222 A | 5/1996 | Ali et al. |
| 5,587,402 A | 12/1996 | Gould et al. |
| 5,602,184 A | 2/1997 | Myers et al. |
| 5,698,219 A | 12/1997 | Valdivia et al. |
| 5,715,810 A | 2/1998 | Armstrong et al. |
| 5,776,445 A | 7/1998 | Cohen et al. |
| 5,785,991 A | 7/1998 | Burkoth et al. |
| 5,800,807 A | 9/1998 | Hu et al. |
| 5,843,468 A | 12/1998 | Burkoth et al. |
| 5,874,063 A | 2/1999 | Briggner et al. |
| 5,882,676 A | 3/1999 | Lee et al. |
| 5,977,186 A | 11/1999 | Franklin |
| 5,983,956 A | 11/1999 | Trofast |
| 6,004,578 A | 12/1999 | Lee et al. |
| 6,006,745 A | 12/1999 | Marecki |
| 6,056,950 A | 5/2000 | Saettone et al. |
| 6,123,068 A | 9/2000 | Lloyd et al. |
| 6,133,324 A | 10/2000 | Imagawa et al. |
| 6,197,934 B1 | 3/2001 | DeVore et al. |
| 6,221,398 B1 | 4/2001 | Jakupovic et al. |
| 6,261,547 B1 | 7/2001 | Bawa et al. |
| 6,268,533 B1 | 7/2001 | Gao et al. |
| 6,313,176 B1 | 11/2001 | Ellinwood, Jr. et al. |
| 6,378,519 B1 | 4/2002 | Davies et al. |
| 7,056,491 B2 | 6/2006 | Gould et al. |
| 7,563,768 B2 | 7/2009 | Nakamura et al. |
| 7,568,480 B2 | 8/2009 | Foley et al. |
| 7,601,355 B2 | 10/2009 | Howard et al. |
| 7,638,549 B2 | 12/2009 | Coleman et al. |
| 2003/0180349 A1 | 9/2003 | Franklin |
| 2004/0087651 A1 | 5/2004 | Pereira Da Fonseca et al. |

(Continued)

FOREIGN PATENT DOCUMENTS

EP 0717987 8/2001

(Continued)

OTHER PUBLICATIONS

Balassiano et al. (2002), "Effects of Perillyl Alcohol in Glial C6 Cell Line in vitro and Anti-Metastatic Activity in Chorioallantoic Membrane Model," *Intern. J. Mol. Med.*, 10:785-788.
Chen et al. (2002), "The Type IV Phosphodiesterase Inhibitor Rolipram Induces Expression of the Cell Cycle Inhibitors p21Cip1 and p27Kip1, Resulting in Growth Inhibition, Increased Differentiation, and Subsequent Apoptosis of Malignant A-172 Glioma Cells," *Cancer Biology & Therapy*, 2002, 1(3):268-276.
Crespi et al. (1986), "Mitoxantrone Affects Topoisomerase Activities in Human Breast Cancer Cells," *Biochem. Biophys. Res. Commun.*, 136(2):521-528.
Crow et al. (1994), "Inhibition of Topoisomerase I by Anthracycline Antibiotics: Evidence for General Inhibition of Topoisomerase I by DNA-Binding Agents," *J. Med. Chem.*, 37(19):3191-3194.
Crowell et al. (1991), "Selective Inhibition of Isoprenylation of 21-26-kDa Proteins by the Anticarcinogen d-Limonene and Its Metabolites," *J. Biol. Chem.*, 266(26): 17679-17685.

(Continued)

*Primary Examiner* — John Ulm
(74) *Attorney, Agent, or Firm* — Foley & Lardner LLP; Antoinette F. Konski

(57) ABSTRACT

This invention provides a compositions for transport of a therapeutic agent. The compositions contain a therapeutic agent and a monoterpene or an analog thereof. In one aspect, the monoterpene is perillyl alcohol (POH) or an analog thereof. In one aspect, the therapeutic agent is provided in an amount effective to treat the disease or subject of choice.

10 Claims, 2 Drawing Sheets

U.S. PATENT DOCUMENTS

| | | |
|---|---|---|
| 2005/0250854 A1 | 11/2005 | Li et al. |
| 2006/0104997 A1 | 5/2006 | Constantinides et al. |
| 2008/0275057 A1 | 11/2008 | Kawabe et al. |
| 2009/0031455 A1 | 1/2009 | Aharoni et al. |
| 2009/0281522 A1 | 11/2009 | Thio et al. |
| 2009/0291894 A1 | 11/2009 | Tezapsidis et al. |
| 2009/0317377 A1 | 12/2009 | Yeomans et al. |
| 2009/0326275 A1 | 12/2009 | DiMauro |
| 2009/0328239 A1 | 12/2009 | Brauner et al. |

FOREIGN PATENT DOCUMENTS

| | | |
|---|---|---|
| WO | WO 92/22286 | 12/1992 |
| WO | WO 95/24895 | 9/1995 |
| WO | WO 97/12687 | 4/1997 |
| WO | WO 99/53901 | 10/1999 |
| WO | WO 99/55319 | 11/1999 |
| WO | WO 00/30614 | 6/2000 |
| WO | WO 00/61108 | 10/2000 |
| WO | WO 03/057193 A1 | 7/2003 |

OTHER PUBLICATIONS

Da Fonseca et al. (2006), "Anaplastic Oligodendroglioma Responding Favorably to Intranasal Delivery of Perillyl Alcohol: A Case Report and Literature Review," Surgical Neurology, 66(6):611-615.

Da Fonseca et al. (2008), "Ras Pathway Activation in Gliomas: A Strategic Target for Intranasal Administration of Perillyl Alcohol," Arch. Immunol. Ther. Exp., 56:267-276.

Da Fonseca et al. (2009), "Correlation of Tumor Topography and Peritumoral Edema of Recurrent Malignant Gliomas with Therapeutic Response to Intranasal Administration of Perillyl Alcohol," Invest. New Drugs, 27(6):557-564.

Denny et al. (2003), "Dual Topoisomerase I/II Inhibitors in Cancer Therapy," Curr. Top. Med. Chem., 3(3):339-353.

Drevs (2003), "PTK/ZK: Novartis," IDrugs, 6(8):787-794.

dtp.nci.nih.gov/docs/misc/common_files/cell_list.html, accessed Feb. 5, 2009.

Encyclopedia of Chemical Technology, Fourth Edition, vol. 23, p. 834-835.

Fernandes et al. (2005), "Perillyl Alcohol Induces Apoptosis in Human Glioblastoma Multiforme Cells," Oncology Reports, 13:943-947.

Foglesong et al. (1992), "Doxorubicin Inhibits Human DNA Topoisomerase I," Cancer Chemother. Pharmacol., 30 (2):123-125.

Gatto et al. (1996), "Identification of Topoisomerase I as the Cytotoxic Target of the Protoberberine Alkaloid Coralyne," Cancer Res., 56(12):2795-2800.

Gonda (1990), "Aerosols for Delivery of Therapeutic and Diagnostic Agents to the Respiratory Tract," Critical Reviews in Therapeutic Drug Carrier Systems, 6(4):273-313.

Gould (1997), "Cancer Chemoprevention and Therapy by Monoterpenes," Environ Health Perspect., 105(Supp 4):977-979.

Hashizume et al. (2008), "New Therapeutic Approach for Brain Tumors: Intranasal Delivery of Telomerase Inhibitor GRN163," Neuro-Oncology, 10(2):112-120.

Hudes et al. (2000), "Phase I Pharmacokinetic Trial of Perillyl Alcohol (NSC 641066) in Patients with Refractory Solid Malignancies," Clinical Cancer Research, 6:3071-3080.

Kasai et al. (1993), "Synthesis of the Enantiomers of Lasiol, An Acyclic Monoterpene Alcohol in the Mandibular Gland Secretion of the Male Ants, Lasius meridionalis," Bioorg. Med. Chem., 1(1):67-70.

Li et al. (2000), "Human Topoisomerase I Poisoning by Protoberberines: Potential Roles for Both Drug-DNA and Drug-Enzyme Interactions," Biochemistry, 39(24):7107-7116.

Makhey et al. (2003), "Substituted Benzo[i]phenanthridines as Mammalian Topoisomerase-Targeting Agents," Bioorg. Med. Chem., 11(8):1809-1820.

McKeage et al. (1997), "Phase I and Pharmacokinetic Study of an Oral Platinum Complex Given Daily for 5 Days in Patients with Cancer," J. Clin. Oneal., 15(7):2691-2700.

Mosmann (1983), "Rapid Colorimetric Assay for Cellular Growth and Survival: Application to Proliferation and Cytotoxicity Assays," 65(1):55-63.

Papamichael (1999), "The Use of Thymidylate Synthase Inhibitors in the Treatment of Advanced Colorectal Cancer: Current Status," The Oncologist, 4:478-487.

Pommier (2006), "Topoisomerase I Inhibitors: Camptothecins and Beyond," Nat. Rev. Cancer, 6(1):789-802.

Pyrko et al. (2007), "The Unfolded Protein Response Regulator GRP78/BiP as a Novel Target for Increasing Chemosensitivity in Malignant Gliomas," Cancer Research, 67:9809-9816.

Pyrko et al. (2007), "HIV-1 Protease Inhibitors Nelfinavir and Atazanavir Induce Malignant Glioma Death by Triggering Endoplasmic Reticulum Stress," Cancer Research, 67: 10920-10928.

Raeburn et al. (1992), "Techniques for Drug Delivery to the Airways, and the Assessment of Lung Function in Animal Models," J. Pharmacol. Toxicol. Methods, 27(3): 143-159.

Ripple et al. (2000), "Phase I Clinical and Pharmacokinetic Study of Perillyl Alcohol Administered Four Times a Day," Clinical Cancer Res., 6:390-396.

Southall et al. (2000), "Developments in Nasal Drug Delivery," Innov. Pharm. Tech. 110-115.

Stratton et al. (2010), "A Phase 2a Study of Topical Perillyl Alcohol Cream for Chemoprevention of Skin Cancer," Cancer Prevention Research, 3: 160-169.

Stupp et al. (2005), "Radiotherapy Plus Concomitant and Adjuvant Temozolomide for Glioblastoma," New England Journal of Medicine, 352(10):987-996.

Thorne et al. (2004), "Delivery of Insulin-Like Growth Factor-I to the Rat Brain and Spinal Cord Along Olfactory and Trigeminal Pathways Following Intranasal Administration," Neuroscience, 127:481-496.

Wen et al. (2008), "Malignant Gliomas in Adults," New England Journal of Medicine, 359(5):492-507.

WHO Specifications and Evaluations for Public Health Pesticides: Malathion, World Health Organization, 2003.

Wikipedia—Benzoate ester, Retrieved on Jul. 26, 2011 from URL: https://commons.wikimedia.orq/wiki/Category:Benzoate_esters: 2 pages.

Wikipedia—Crystallization, Retrieved on Jul. 6, 2011: 6 pages.

Wikipedia—Ester, Retrieved on Jul. 8, 2011 from URL: http://en.wikipedia.org/wiki/Ester: 7 pages.

Wikipedia—Recrystallization from URL: http://en.wikipedia.org/wiki/Recrystallization_(chemistry): 7 pages.

Wikipedia—Separation Process, Retrieved on Feb. 11, 2011 from URL: http://en.wikipedia.org/wiki/Separation_of_mixtures.

Wiseman et al. (2007), "Cell Cycle Arrest by the Isoprenoids Perillyl Alcohol, Geraniol and Farnesol Is Mediated by p21Cip1 and p27Kip1 in Human Pancreatic Adenocarcinoma Cells," J. Pharamcol. Exp. Thera., 320(3): 1163-1170.

Xu et al. (1998), "DNA Minor Groove Binding-Directed Poisoning of Human DNA Topoisomerase I by Terbezimidazoles," Biochemistry, 37(10):3558-3566.

Cerda et al. (1994) "Enhanced antitumor of lovastatin and peryllyl alcohol combinations in the colonic adenocarcinoma cell line SW 480" Proceedings of the Annual Meeting of the American Association for Cancer Research, 35:335.

Da Fonseca et al. (2008) "Preliminary results from a phase I/II study of perillyl alcohol intranasal administration in adults with recurrent malignant gliomas" Surgical Neurology 70:259-267.

THERAPEUTIC COMPOSITIONS COMPRISING MONOTERPENES

CROSS-REFERENCE TO RELATED APPLICATIONS

This application claims the benefit under 35 U.S.C. §119 (e) of U.S. Provisional application Ser. No. 61/150,714, filed Feb. 6, 2009, the contents of which is hereby incorporated by reference in its entirety.

BACKGROUND

Despite the development of drugs that preferentially target tumor cells without harming normal tissues, delivery of these drugs to brain tumors remains a major challenge because of difficulty in penetrating the blood-brain barrier (BBB). Astrocytomas are the most common group of primary brain tumors. Grade III astrocytomas or anaplastic astrocytomas (AA), and grade IV astrocytomas, or glioblastoma multiforme (GBM) tumors have a poor prognosis due to their aggressive growth and resistance to available therapies. Present therapies rely on early detection and the standard treatment of AA and GBM still consists of surgical resection, radiation therapy and chemotherapy. Although chemotherapy may increase the survival of patients with low grade gliomas to 5 to 10 years, this increase is only a couple of months in cases of GBM. GBMs are among the most lethal and intractable of human tumors, and drug resistance is one of the major obstacles to their successful treatment. Until now, no therapeutic modality has substantially changed the outcome of patients with GBM, which is therefore considered incurable. Hashizume et al. (2008) Neuro-Oncology 10:112-120.

Clearly there is a great need for new therapeutic strategies that will provide efficient drug delivery to the brain tumors and other cancers that require delivery of therapeutic agents across the BBB. This invention satisfies this need and provides related advantages as well.

SUMMARY OF THE INVENTION

This invention provides a compositions for transport of a therapeutic agent. The compositions comprise, or alternatively consist essentially of, or yet further consist of a therapeutic agent and a monoterpene or an analog thereof. In one aspect, the monoterpene is perillyl alcohol (POH) or an analog thereof. In one aspect, the compositions further comprise, or alternatively consist essentially of, or yet further consist of an effective amount of a co-solvent. In one aspect, the therapeutic agent is provided in an amount effective to treat the disease or subject of choice. In a yet further aspect, the composition further comprises, or alternatively consists essentially of, or yet further consists of, a pharmaceutically acceptable carrier.

In one specific embodiment, the composition comprises, or alternatively consists essentially of, or yet further consists of a therapeutic agent, at least about 0.03% (v/v) of a monoterpene such as perillyl alcohol or an analog thereof; at least about 2.6% total of a co-solvent which can be 1.3% (v/v) of a polyol such as glycerol or an equivalent thereof; and at least about 1.3% of ethanol or an equivalent thereof (v/v; 96% ethanol). In a further aspect, the compositions further comprise, or alternatively consist essentially of, or yet further consist of, a permeation enhancer or pharmaceutically acceptable carrier.

The composition of this invention can be formulated for administration intranasally as a spray or in a drop; transdermally via a transdermal patch or iontorphoresis; ocularly or by inhalation using a nebulizer or similar device.

In one aspect, the therapeutic agent is an anticancer drug. For the purpose of illustration only, the anticancer drug in the composition is one or more of a DNA alkylating agent (temozolomide, BCNU), a topoisomerase inhibitor (i.e. irinotecan), an endoplasmic reticulum stress inducing agent (i.e. celecoxib, dimethyl-celecoxib or a boron radiosensitizers (i.e. velcade).

The invention also provides a method for inhibiting the growth of a cell such as a cancer cell by contacting the cell with an effective amount of the composition as described herein. The contacting can be in vitro or in vivo. The invention also provides a method for inhibiting the growth of a cell, such as a cancer cell, in a subject in need thereof by administering to the subject a composition described herein under conditions that inhibit the growth of the cell.

In one aspect, the cell is one or more of a primary central nervous system (CNS) tumor cell (gliomas, menengiomas, pituitary adenomas), a CNS cancer cell metastasis from a systemic cancer, lung cancer cell, prostate cancer cell, breast cancer cell, hematopoietic cancer cell or ovarian cancer cell.

This invention also provides a method for treating a disease in a subject in need of such treatment comprising, or alternatively consisting essentially of, or yet further consisting of, administering to the subject an effective amount of the composition as described herein to the subject, thereby treating the disease. In one aspect, the disease to be treated is a neurological disorder or one affecting the central nervous system (CNS). Such diseases include, but are not limited to a primary central nervous system (CNS) tumor (gliomas, menengiomas, pituitary adenomas) or a CNS metastasis from a systemic cancer. Other diseases, include, but are not limited to a cancer such as one or more of lung cancer, prostate cancer, breast cancer, hematopoietic cancer or ovarian cancer.

This invention also provides the compositions as described above for transdermal administration. As such, the compositions can further comprise, or alternatively consist essentially of, or yet further consist of, a permeation or penetration enhancer, a plasticizer, or the like making the composition suitable for transdermal administration. In one aspect, the invention is a transdermal reservoir having within it an effective amount of a composition of this invention for transdermal administration of the composition. In a further aspect, the invention provides a transdermal device containing the transdermal reservoir. The transdermal reservoir and/or device can be used to administer an effective amount of the composition of this invention to a subject in need of treatment. These devices are suitable to administer pain medications such as analgesics and narcotics. Examples of these therapeutic agents are provided below.

This invention also provides the compositions as described above for intranasal administration. As such, the compositions can further comprise, or alternatively consist essentially of, or yet further consist of, a permeation or penetration enhancer or the like making the composition suitable for intranasal administration. In one aspect, the invention is an intranasal formulation having within it an effective amount of a composition of this invention. These formulations are suitable for delivery of cancer drugs or drugs to treat neurological disorders or cancers. Examples of these drugs are provided below.

This invention also provides the compositions as described above for administration by inhalation. As such, the compositions can further comprise, or alternatively consist essentially of, or yet further consist of, a permeation or penetration enhancer or the like making the composition suitable for administration by inhalation. In one aspect, the invention is formulation for administration by inhalation having within it an effective amount of a composition of this invention for inhalation of the composition. These formulations are suitable to administer cancer drugs or drugs to treat neurological disorders. Examples of these drugs are provided below.

Also provided by this invention is a kit comprising the composition as described above formulated for administration by inhalation and a device for administering the composition by inhalation and instruction for use.

The compositions are provided to enhance the activity of therapeutic agents, especially those whose site of activity is across a endothelial cell layer such as the stratum corneum and the blood brain barrier.

The compositions of this invention are useful for the manufacture of medicaments that must pass across an endothelial cell layer, such as the stratum corneum of the skin, the lung tissue, the eye, the nasal cavity and the blood brain barrier. Thus, in one aspect the invention provides a method for treating a disease effecting the central nervous system, comprising, or alternatively consisting essentially of, or yet further consists of, administering an effective amount of the compositions described above, thereby treating the disease. For the purpose of illustration only, such diseases include, but are not limited to one or more of the group consisting of head and neck cancers, multiple sclerosis, Alzheimer's Disease, meningitis, epilepsy, neuromyelitis optica (Devic's disease), late-stage neurological trypanosomiasis (Sleeping Sickness), progressive multifocal leukoencephalopathy (PML), De Vivo disease (GLUT1 deficiency syndrome), HIV encephalitis, glioblastoma, lung cancer, melanoma, malignant gliobastoma, anaplastic astrocytoma or anaplastic oligodendroglioma. When the disease to be treated is gliobastoma or malignant glioblastoma, the therapeutic agent in the composition can comprise, or alternatively consist essentially of, or yet further consist of temozolomide or dimethyl-celecoxib.

When the drug is to be administered transdermally, the composition can be formulated for topical administration in a gel or lotion or contained within a transdermal reservoir, such as a polymer matrix or liquid reservoir. These formulations can additionally comprise, or alternatively consist essentially of, or yet further consist of a permeation or penetration enhancer or plasticizer.

When the drug is to be inhaled for administration, the invention further provides a kit comprising, or alternatively consisting essentially of or yet further consists of, any of compositions as described above a device for administering the composition by inhalation and instruction for use.

When the drug is to be inhaled for ocular delivery, the invention further provides a kit comprising, or alternatively consisting essentially of or yet further consists of, any of compositions as described above and instruction for use.

The invention also provides for determining if a therapeutic agent is a potential drug candidate, such as for the treatment of cancer, by contacting a first sample of cells with an effective amount of a composition described herein and a second sample of cells with an amount of the therapeutic agent, determining if the growth of the first and second cell samples are inhibited, wherein if the growth of the second sample is substantially the same or greater than the first sample, then the therapeutic agent is a potential drug for therapy. The contacting can be in vitro or in vivo.

DETAILED DESCRIPTION OF THE INVENTION

Figure 1:
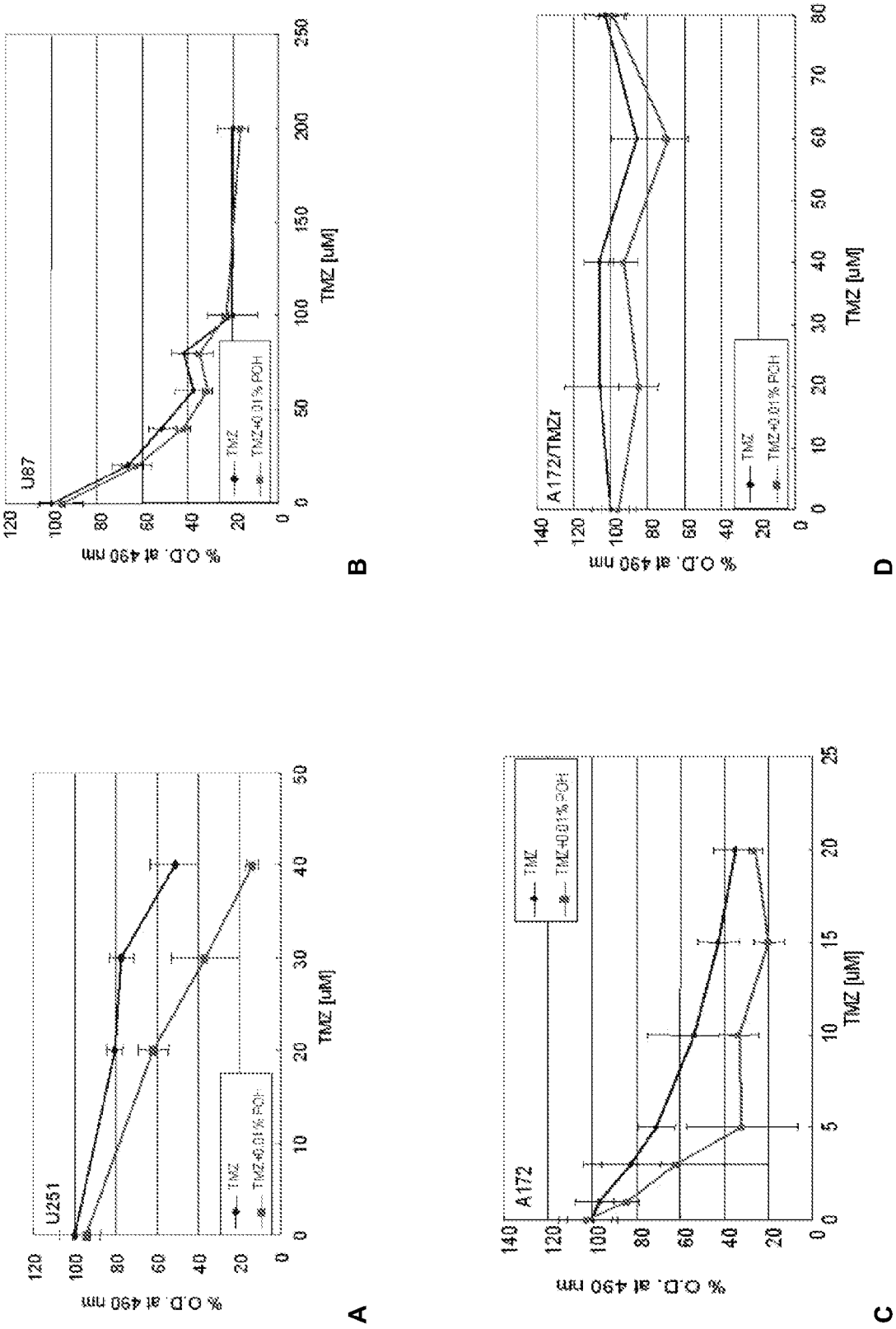
FIG. 1, Panels A through D, show a composition comprising POH and temozolamide (TMZ) induces greater cytoxicity in glioma cells than POH or TMZ alone.

Throughout this application, the text refers to various embodiments of the present compositions and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Definitions

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients. Embodiments defined by each of these transition terms are within the scope of this invention.

All numerical designations, e.g., pH, temperature, time, concentration, and molecular weight, including ranges, are approximations which are varied (+) or (−) by increments of 0.1 or 1.0 as is appropriate. It is to be understood, although not always explicitly stated that all numerical designations are preceded by the term "about" which includes a standard deviation of about 15%, or alternatively about 10% or alternatively about 5%. It also is to be understood, although not always explicitly stated, that the reagents described herein are merely exemplary and that equivalents of such are known in the art.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. Studies in animal models generally may be used for guidance regarding effective dosages for treatment of diseases. In general, one will desire to administer an amount of the compound that is effective to achieve a serum level commensurate with the concentrations found to be effective in vitro. Thus, where a compound is found to demonstrate in vitro activity, for example as noted in the Tables discussed below one can extrapolate to an effective dosage for administration in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response treating a glioblastoma.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Preferred are compounds that are potent and can be administered locally at very low doses, thus minimizing systemic adverse effects.

Monoterpenes as used herein intend the class of terpenes that consist of two isoprene units and have the molecular formula $C_{10}H_{16}$ such as perillyl alcohol, as well as obvious modifications such as oxidation or rearrangement and pharmaceutically acceptable salts thereof. In general, monoterpenes may be linear (acyclic) or contain rings. Biochemical modifications such as oxidation or rearrangement produce monopterenoids. Examples of monoterpenes and monopternoids for use in this invention include perillyl alcohol (S(−)) and R (+)), geranyl pyrophosphate, ocimene, myrcene, geraniol, citral, citronellal, linalool, limonene, terpinenes, phellandrenes, terpinolene; the terpenoids such as p-cymene which is derived from monocyclic terpenes such as menthol, thymol and carvocrol; bicyclic monoterpenes such as pinene, carene, sabinene, camphene, thujene; bicyclic monoterpenoids such as camphor, borneol and eucalyptol.

In one aspect, the monoterpene for use in this invention is perillyl alcohol or analog thereof. Perillyl alcohol is a naturally occurring monoterpene related to limonene with antineoplastic activity. Perillyl alcohol inhibits farnesyl transferase and geranylgeranyl transferase, thereby preventing post-translational protein farnesylation and isoprenylation and activation of oncoproteins such as p21-ras, and arresting tumor cells in the G1 phase of the cell cycle. Perillyl alcohol (commonly abbreviated as POH) is also known in the art as dihydrocuminyl alcohol, perilla alcohol, perillic alcohol, perillol, (S)-(−)-perillyl alcohol, 1-cyclohexene-1-methanol, 4-(1-methylethenyl)-1-cyclohexene-1-methanol, 4-isopropenylcyclohex-1-ene-1-methanol, p-mentha-1,8-dien-7-ol. See The National Cancer Institute's web page for a description of the pharmacology of POH as well as current and past drug trials.

Analogs of POH for use in this invention include, but are not limited to perrilaldehyde (PALD) and carboxylic acid esters of POH as described in U.S. Pat. No. 3,957,856.

The term "active agent" or "therapeutic agent" as used to describe the principal active ingredient of the composition intends a biologically active compound or mixture of compounds that has a therapeutic, prophylactic or other beneficial pharmacological and/or physiological effect for the intended purpose. Examples of types of drugs that may be used in the composition include, but are not limited to drugs whose systemic delivery to the affected tissue has been hampered by the blood brain barrier, such as drugs to treat gliomas.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present invention is also useful for veterinary treatment of companion mammals, exotic animals and domesticated animals, including mammals, rodents, and the like.

The term administration shall include without limitation, administration by ocular, oral, parenteral (e.g., intramuscular, intraperitoneal, inhalation, transdermal intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, ocular etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

A "pathological cell" is one that is pertaining to or arising from disease. Pathological cells can be hyperproliferative. A "hyperproliferative cell" means cells or tissue are dividing and growing at a rate greater than that when the cell or tissue is in a normal or healthy state. Examples of such include, but are not limited to cancer cells. Hyperproliferative cells also include de-differentiated, immortalized, neoplastic, malignant, metastatic, and cancer cells such as sarcoma cells, leukemia cells, carcinoma cells, or adenocarcinoma cells. Specified cancers include, but are not limited to lung cancer cells, glioblastoma cells, and esophageal carcinoma cells.

A "control" is an alternative subject or sample used in an experiment for comparison purpose. A control can be "positive" or "negative". For example, where the purpose of the experiment is to determine a correlation of the efficacy of a composition of the invention for the treatment for a particular type of disease or cancer, it is generally preferable to use a positive control (a compound or composition known to exhibit the desired therapeutic effect) and a negative control (a subject or a sample that does not receive the therapy or receives a placebo).

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modern usage generally denotes a neoplasm. The suffix "-oma" means tumor and usually denotes a benign neoplasm, as in fibroma, lipoma, and so forth, but sometimes implies a malignant neoplasm, as with so-called melanoma, hepatoma, and seminoma, or even a non-neoplastic lesion, such as a hematoma, granuloma, or hamartoma. The suffix "-blastoma" denotes a neoplasm of embryonic cells, such as neuroblastoma of the adrenal or retinoblastoma of the eye.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues. One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

"Suppressing" tumor growth indicates a growth state that is curtailed compared to growth without any therapy. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

Description Of The Embodiments
Compositions of this Invention

This invention provides compositions for transport of a therapeutic agent. The compositions comprise, or alternatively consist essentially of, or yet further consist of a therapeutic agent and a monoterpene or an analog of the monoterpene. In one aspect, the monoterpene is perillyl alcohol (POH) or an analog thereof. In one aspect, the therapeutic agent is provided in an amount effective to treat the disease or subject of choice. Examples of the therapeutic agents are provided infra. In a yet further aspect, the composition further comprises, or alternatively consists essentially of, or yet further consists of, any one or more of a pharmaceutically acceptable carrier, a solubility enhancer or a polyol.

In one aspect, the monoterpene or the analog thereof comprises, or alternatively consists essentially of, or yet further consists of from about 0.0001% ($10^{-4}$) (v/v) to about 50% of the total composition, or alternatively from about 0.001% ($10^{-3}$) (v/v) to about 40% of the total composition, or alternatively from about 0.001% ($10^{-2}$) (v/v) to about 30% of the total composition or alternatively from about 0.01% (v/v) to about 20% of the total composition, or alternatively from about 0.01% (v/v) to about 10% of the total composition, or alternatively from about 0.01% (v/v) to about 5% of the total composition, or alternatively from about 0.05% (v/v) to about 3% of the total composition, or alternatively from about 0.04% (v/v) to about 2% of the total composition, or alternatively from about 0.1% (v/v) to about 0.4% (v/v), or alternatively about 0.015% (v/v), or alternatively about 0.02% (v/v), or alternatively about 0.03% (v/v), or alternatively about 0.04% (v/v).

In one aspect, the monoterpene is POH or an analog thereof and the composition comprises, or alternatively consists essentially of, or yet further consists of POH or the analog thereof from about 0.0001% ($10^{-4}$) (v/v) to about 50% of the total composition, or alternatively from about 0.001% ($10^{-3}$) (v/v) to about 40% of the total composition, or alternatively from about 0.001% ($10^{-2}$) (v/v) to about 30% of the total composition or alternatively from about 0.01% (v/v) to about 20% of the total composition, or alternatively from about 0.01% (v/v) to about 10% of the total composition, or alternatively from about 0.01% (v/v) to about 5% of the total composition, or alternatively from about 0.05% (v/v) to about 3% of the total composition, or alternatively from about 0.04% (v/v) to about 2% of the total composition, or alternatively from about 0.1% (v/v) to about 0.4% (v/v), or alternatively about 0.015% (v/v), or alternatively about 0.02% (v/v), or alternatively about 0.03% (v/v), or alternatively about 0.04% (v/v).

Additional components can comprise, or alternatively consist essentially of, or yet further consist of, the compositions.

The additional components include, but are not limited to polyols which may also act as a permeation enhancer or co-solvent as does ethanol. Suitable permeation enhancers include but are not limited to fatty acid esters of glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA), lauryl pyroglutamate (LP), glyceryl monolaurate (GML), glyceryl monocaprylate, glyceryl monocaprate, glyceryl monooleate (GMO) and sorbitan monolaurate. The patent literature also describes permeation enhancers known to those of skill in the art. See U.S. Pat. Nos. 5,785,991; 5,843,468; 5,882,676; and 6,004,578.

The (v/v) percentage of the co-solvent is from about 0.1% to about 20%, or alternatively from about 0.15% to about 16%, or alternatively from about 0.2% to about 16%, or alternatively from about 1.0% to about 8%, or alternatively from about 2.0% to about 3.0%, or alternatively from about 2.4% to about 5%, or alternatively about 1.0%, or alternatively about 1.5%, or alternatively about 2.0%, or alternatively about 2.1%, or alternatively about 2.5%, or alternatively about 2.7%, or alternatively about 3.0%, or alternatively about 4.0%, or alternatively about 5%, of the total composition.

Co-solvents are known in the art and include without limitation glycerol, glycol, ethanol, methanol, propanol, isopropanol, butanol and the like.

When the co-solvent is glycerol or an equivalent of glycerol, typical ranges in the composition include from about 0.1% to about 10% of the permeation enhancer such as glycerol, or alternatively from about 0.15% to about 8%, or alternatively from about 0.2% to about 6%, or alternatively from about 0.5% to about 4%, or alternatively from about 1.0% to about 1.5%, or alternatively from about 1.3% to about 2%, or alternatively about 1.0%, or alternatively about 1.1%, or alternatively about 1.2%, or alternatively about 1.3%, or alternatively about 1.4%, or alternatively about 1.5%, or alternatively about 1.6%, each of the total composition.

The (v/v) percentage of ethanol or an equivalent of ethanol can vary but typical ranges include from about 0.1% to about 10% of the solubility enhancer such as ethanol, or alternatively from about 0.15% to about 8%, or alternatively from about 0.2% to about 6%, or alternatively from about 0.5% to about 4%, or alternatively from about 1.0% to about 1.5%, or alternatively from about 1.3% to about 2%, or alternatively about 1.0%, or alternatively about 1.1%, or alternatively about 1.2%, or alternatively about 1.3%, or alternatively about 1.4%, or alternatively about 1.5%, or alternatively about 1.6%, each of the total composition.

In one specific embodiment, the composition comprises, or alternatively consists essentially of, or yet further consists of an effective amount of a therapeutic agent. Suitable therapeutic agents include, but are not limited to chemotherapeutic compounds such as DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, antibiotics, boron radiosensitizers (i.e. velcade) and chemotherapeutic combination therapies. Non-limiting examples of chemotherapeutic agents and therapeutic agents are provided here. Chemical and biological equivalents of these agents are within the scope of this invention.

In one aspect of the invention, the anticancer drug is a DNA alkylating agent which attaches an alkyl group to DNA. Such agents are well known in the art and are used to treat a variety of tumors. Non-limiting examples of a DNA alkylating agents are Nitrogen mustards, such as Mechlorethamine, Cyclophosphamide (Ifosfamide, Trofosfamide), Chlorambucil (Melphalan, Prednimustine), Bendamustine, Uramustine and Estramustine; Nitrosoureas, such as Carmustine (BCNU), Lomustine (Semustine), Fotemustine, Nimustine, Ranimustine and Streptozocin; Alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

In another aspect of the invention, the anticancer drug is a platinum based compound which is a subclass of DNA alkylating agents. Such agents are well known in the art and are used to treat a variety of cancers, such as, lung cancers, head and neck cancers, ovarian cancers, colorectal cancer and prostate cancer. Non-limiting examples of such agents include Carboplatin, Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"Oxaliplatin" (Eloxatin®) is a platinum-based chemotherapy drug in the same family as cisplatin and carboplatin. It is typically administered in combination with fluorouracil and leucovorin in a combination known as FOLFOX for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include without limitation cisplatin, carboplatin, aroplatin, lobaplatin, nedaplatin, and JM-216 (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

In one aspect of the invention, the anticancer drug is a topoisomerase inhibitor which is an agent that interferes with the action of topoisomerase enzymes (topoisomerase I and II). Topoisomerases are enzymes that control the changes in DNA structure by catalyzing the breaking and rejoining of the phosphodiester backbone of DNA. Such agents are well known in the art. Non-limiting examples of Topoisomerase I inhibitors include Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and U.S. Patent Appl. No. 2005/0250854; Protoberberine alkaloids and derivatives thereof including berberrubine and coralyne as described in Li et al. (2000) Biochemistry 39(24): 7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8.

In one aspect of the invention, the topoisomerase I inhibitors can be selected from the group of, but not limited to, Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and US Patent Appl. No. 2005/0250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8, will be used in combination therapy with antibody based chemotherapy described above to treat patients identified with the appropriate genetic markers.

Irinotecan (CPT-11) is sold under the tradename of Camptosar®. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

In another aspect, some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

In one aspect of the invention, Topoisomerase II inhibitors include, but are not limited to Etoposide and Teniposide.

In another aspect of the invention, dual topoisomerase I and II inhibitors selected from the group of, but not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, and Anthracenyl-amino Acid Conjugates as described in Denny and Baguley (2003) Curr. Top. Med. Chem. 3(3):339-353. In one aspect, they can be used in combination therapy with antibody based chemotherapy described above to treat patients identified with the appropriate genetic markers.

"Lapatinib" (Tykerb®) is an oncolytic dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SU11248) and leflunomide (SU101).

A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

In one aspect of the invention, the therapeutic agent is an endoplasmic reticulum stress inducing agent. Examples of such agents include, but are not limited to, Celecoxib, dimethyl-celecoxib and boron radiosensitizers (i.e. valcade (Bortezomib)).

In another aspect of the invention, the anticancer drug is an antimetabolite agent which inhibits the use of a metabolite, i.e. another chemical that is part of normal metabolism. In cancer treatment, antimetabolites interfere with DNA production, thus cell division and growth of the tumor. Non-limiting examples of these agents are Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU).

Fluorouracil (5-FU) belongs to the family of therapy drugs call pyrimidine based anti-metabolites. 5-FU is transformed into different cytotoxic metabolites that are then incorporated into DNA and RNA thereby inducing cell cycle arrest and apoptosis. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Capecitabine and Tegafur are examples of chemical equivalents of 5-FU. It is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®.

Leucovorin (Folinic acid) is an adjuvant used in cancer therapy. It is used in synergistic combination with 5-FU to improve efficacy of the chemotherapeutic agent. Without being bound by theory, addition of Leucovorin is believed to enhance efficacy of 5-FU by inhibiting thymidylate synthase. It has been used as an antidote to protect normal cells from high doses of the anticancer drug methotrexate and to increase the antitumor effects of fluorouracil (5-FU) and tegafur-uracil. It is also known as citrovorum factor and Wellcovorin. This compound has the chemical designation of L-Glutamic acid N[4[[(2amino-5-formyl1,4,5,6,7, 8hexahydro4oxo 6-pteridinyl)methyl]amino]benzoyl], calcium salt (1:1).

Examples of vincalkaloids, include, but are not limited to vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); Proteasome inhibitor (Bortezomib); Phosphodiesterase inhibitor (Anagrelide); IMP dehydrogenase inhibitor (Tiazofurine); and Lipoxygenase inhibitor (Masoprocol).

Examples of tyrosine kinase inhibitors include, but are not limited to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib); FLT3 (Lestaurtinib); PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-, butanedioate (1:1). Synonyms and analogs of PTK/ZK are known as Vatalanib, CGP79787D, PTK787/ZK 222584, CGP-79787, DE-00268, PTK-787, PTK-787A, VEGFR-TK inhibitor, ZK 222584 and ZK.

Examples of antibiotics include, but are not limited to actinomycin, Bleomycin, Mitomycin, Plicamycin.

Examples of receptor antagonists include, but are not limited to ERA (Atrasentan); retinoid X receptor (Bexarotene); and a sex steroid (Testolactone).

Examples of chemotherapeutic agents and combination therapies include, but are not limited to amsacrine, Trabectedin, retinoids (Alitretinoin, Tretinoin), Arsenic trioxide, asparagine depleter (Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from the National Comprehensive Cancer Network's web site, nccn.org, last accessed on May 27, 2008.

Examples of therapeutic antibodies include, but are not limited to anti-HER1/EGFR (Cetuximab, Panitumumab); Anti-HER2/neu (erbB2) receptor (Trastuzumab); Anti-Ep-CAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab), as well as biological equivalents thereof.

Bevacizumab is sold under the trade name Avastin by Genentech. It is a humanized monoclonal antibody that binds to and inhibits the biologic activity of human vascular endothelial growth factor (VEGF). Biological equivalent antibodies are identified herein as modified antibodies and those which bind to the same epitope of the antigen, prevent the interaction of VEGF to its receptors (Flt01, KDR a.k.a. VEGFR2) and produce a substantially equivalent response, e.g., the blocking of endothelial cell proliferation and angiogenesis.

In one aspect, the "chemical equivalent" means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

In one aspect, the "biological equivalent" means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody. An example of an equivalent Bevacizumab antibody is one which binds to and inhibits the biologic activity of human vascular endothelial growth factor (VEGF).

Formulations

The pharmaceutical compositions can be administered by any one of the following routes: ocular, oral, systemic (e.g., transdermal, intranasal or by suppository), or parenteral (e.g., intramuscular, intravenous or subcutaneous) administration. In some embodiments, the manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of described herein is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI), mouth mask and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI can dispense therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

For ocular administration, the compositions described herein can be formulated as a solution, emulsion, suspension, etc., suitable for administration to the eye. A variety of vehicles suitable for administering compounds to the eye are known in the art. Specific non-limiting examples are described in U.S. Pat. Nos. 6,261,547, 6,197,934, 6,056,950, 5,800,807, 5,776,445, 5,698,219, 5,521,222, 5,403,841, 5,077,033, 4,882,150, and 4,738,851.

The compositions can additional contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

Compressed gases may be used to disperse a composition described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the composition in a formulation can vary within the full range employed by those skilled in the art. Typically, the formulation will contain, on a volume percent (v/v %) basis, from about 0.01-99.99 v/v % of a composition described herein based on the total formulation, with the balance being one or more suitable pharmaceutical excipients. In some embodiments, the composition is present at a level of about 1-80 v/v %.

Thus, the composition of this invention can be formulated for administration intranasally as a spray or in a drop; transdermally via a transdermal patch or iontorphoresis and by inhalation using a nebulizer, MDI or similar device. As such, the compositions can further comprise, or alternatively consist essentially of, or yet further consist of, a permeation or penetration enhancer, a plasticizer, or the like making the composition suitable for transdermal administration. In one aspect, the invention is a transdermal reservoir having within it an effective amount of a composition of this invention for transdermal administration of the composition. In a further aspect, the invention provides a transdermal device containing the transdermal reservoir. The transdermal reservoir and/or device can be used to administer an effective amount of the composition of this invention to a subject in need of treatment. These devices are suitable to administer pain medications such as analgesics and narcotics. Examples of these therapeutic agents are provided supra.

This invention also provides the compositions as described above for intranasal administration. As such, the compositions can further comprise, or alternatively consist essentially of, or yet further consist of, a permeation or penetration enhancer or the like making the composition suitable for intranasal administration. In one aspect, the invention is an intranasal formulation having within it an effective amount of a composition of this invention for intranasal administration of the composition. These formulations are suitable to cancer drugs or drugs to treat neurological disorders. Examples of these drugs are provided below.

This invention also provides the compositions as described above for administration by inhalation. As such, the compositions can further comprise, or alternatively consist essentially of, or yet further consist of, a permeation or penetration enhancer or the like making the composition suitable for administration by inhalation. In one aspect, the invention is formulation for administration by inhalation having within it an effective amount of a composition of this invention for inhalation of the composition. These formulations are suitable to administer cancer drugs or drugs to treat neurological disorders. Examples of these drugs are provided supra.

In Vitro and in Vivo Methods

Pathological cells, tissues and pathologies characterized by pathological cells such as hyperproliferative or cells are treated by contacting the cells or tissue associated with these pathologies with an effective amount of a composition of this invention. The cells, such as cancer cells can be primary cancer cells or can be cultured cells available from tissue banks such as the American Type Culture Collection (ATCC). The pathological cells can comprise or consist essentially of or consist of gliomas, menengiomas, pituitary adenomas, or a CNS metastasis from a systemic cancer. Other pathological cells include, but are not limited to a cancer is one or more of lung cancer, prostate cancer, breast cancer, hematopoietic cancer or ovarian cancer.

The cells can be of any appropriate type, which includes for example, vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human.

The contacting can be any one or more of in vitro, ex vivo and in vivo. The contacting can be at an effective temperature which includes but is not limited to temperatures in the range of about 40° F. to about 120° F., or alternatively from about 50° F. to about 115° F., or alternatively from about 60° F. to about 100° F., or alternatively from about 65° F. to about 95° F., or alternatively from about 65° F. to about 115° F. or alternatively from about 65° F. to about 115° F. or alternatively from about 68° F. to about 110° F., or alternatively from about 68° F. to about 100° F., or alternatively from about 70° F. to about 95° F., or alternatively from about 72° F. to about 90° F., or alternatively from about 75° F. to about 85° F., or alternatively from about 75° F. to about 80° F., or alternatively at least 50° F., or alternatively from about 55° F., or alternatively at least 60° F., or alternatively at least 70° F., or alternatively from about 72° F., or alternatively at least 75° F., or alternatively at least 80° F., or alternatively at least 85° F., or alternatively at least 90° F., or alternatively at least 95° F., or alternatively at least 98° F., or alternatively at least 100° F., or alternatively at least 102° F., or alternatively at least 105° F. When contacting is in vivo, the contacting can be in singular or multiple administrations and by multiple routes (e.g., intranasally, ocularly or inhalation) as determined by the treating physician. When contacting is in vitro, the contacting can be in cell culture, e.g., the cells are cultured human malignant glioma cell lines U87 and A172 cells (obtainable from the American Type Culture Collection), or they can be from an animal biopsy. Examples of cell culturing and assay conditions as well as methods for delivery of drugs to patients and animal models are known in the art and provided in the experimental examples provided infra (U.S. Patent Appl. No. 2004/0087651, (published May 6, 2004), Balassiano et al. (2002) Intern. J. Mol. Med. 10:785-788; Thorne et al. (2004) Neuroscience 127:481-496; Fernandes et al. (2005) Oncology Reports 13:943-947; da Fonseca et al. (2006) 66:611-615; da Fonseca et al. (2008) Surgical Neurology 70:259-267; da Fonseca et al. (2008) Arch. Immunol. Ther. Exp. 56:267-276 and Hashizume et al. (2008) Neuroncology 10:112-120, each incorporated by reference).

When practiced in vivo in a subject other than a human patient such as a mouse, the method provides an animal model for use in discovering alternative agents, compositions and therapies. In a human patient, the method treats pathologies as described above or as characterized by hyperproliferative cells, e.g., cancer. Methods for detecting clinical and sub-clinical evidence of effective therapy are known in the art and described in U.S. Patent Appl. No. 2004/0087651, (published May 6, 2004), Balassiano et al. (2002) Intern. J. Mol. Med. 10:785-788; Thorne et al. (2004) Neuroscience 127: 481-496; Fernandes et al. (2005) Oncology Reports 13:943-947; da Fonseca et al. (2006) 66:611-615; da Fonseca et al. (2008) Surgical Neurology 70:259-267; da Fonseca et al. (2008) Arch. Immunol. Ther. Exp. 56:267-276 and Hashizume et al. (2008) Neuroncology 10:112-120, each incorporated by reference. In each of these methods, an effective amount of a composition of this invention is delivered or administered to the subject, e.g., mouse or human patient.

This invention also provides a method for treating a disease in a subject in need of such treatment comprising, or alternatively consisting essentially of, or yet further consisting of, administering to the subject an effective amount of the composition as described herein to the subject, thereby treating the disease. In one aspect, the disease to be treated is a neurological disorder or one affecting the central nervous system (CNS). Such diseases include, but are not limited to a primary central nervous system (CNS) tumor (gliomas, menengiomas, pituitary adenomas) or a CNS metastasis from a systemic cancer. Other diseases, include, but are not limited to a cancer is one or more of lung cancer, prostate cancer, breast cancer, hematopoietic cancer or ovarian cancer.

The compositions can be administered to an animal or mammal by a treating veterinarian.

Co-Administration

Co-administration of these compositions can be administered concurrently or sequentially with other therapies such as radiation therapy, as known to those of skill in the art. The use of operative combinations is contemplated to provide therapeutic combinations that may lower total dosage of each component than may be required when each individual therapeutic method or composition is used alone. A reduction in adverse effects may also be noted. Thus, the present invention also includes methods involving co-administration of the compositions described herein with one or more additional active agents or methods. Indeed, it is a further aspect of this invention to provide methods for enhancing other therapies and/or pharmaceutical compositions by co-administering a composition of this invention. In co-administration procedures, the agents may be administered concurrently or sequentially. In one embodiment, the compounds described herein are administered prior to the other active agent(s), therapy or therapies. The pharmaceutical formulations and modes of administration may be any of those described herein or known to those of skill in the art.

Use of Compounds for Preparing Medicaments

The compositions of the present invention are also useful in the preparation of medicaments to treat a variety of pathologies as described above. The methods and techniques for preparing medicaments of a composition are known in the art. For the purpose of illustration only, pharmaceutical formulations and routes of delivery are detailed below.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Pharmaceutical Delivery

Various delivery systems are known and can be used to administer a composition of the invention, e.g., intranasally or by inhalation, and the like. To determine patients that can be beneficially treated, a tissue sample can be removed from the patient and the cells are assayed for sensitivity to the agent.

Therapeutic amounts can be empirically determined and will vary with the pathology being treated, the subject being treated and the efficacy and toxicity of the composition as well as whether the composition is used alone or in combination with other agents of therapeutic methods. When delivered to an animal, the method is useful to further confirm efficacy of the agent.

Administration in vitro or in vivo can be effected in one dose, continuously or intermittently throughout the course of treatment and at various temperatures. Suitable temperature ranges include temperatures in the range of about 40° F. to about 120° F., or alternatively from about 50° F. to about 115° F., or alternatively from about 60° F. to about 100° F., or alternatively from about 65° F. to about 95° F., or alternatively from about 65° F. to about 115° F. or alternatively from about 65° F. to about 115° F. or alternatively from about 68° F. to about 110° F., or alternatively from about 68° F. to about 100° F., or alternatively from about 70° F. to about 95° F., or alternatively from about 72° F. to about 90° F., or alternatively from about 75° F. to about 85° F., or alternatively from about 75° F. to about 80° F., or alternatively at least 50° F., or alternatively from about 55° F., or alternatively at least 60° F., or alternatively at least 70° F., or alternatively from about 72° F., or alternatively at least 75° F., or alternatively at least 80° F., or alternatively at least 85° F., or alternatively at least 90° F., or alternatively at least 95° F., or alternatively at least 98° F., or alternatively at least 100° F., or alternatively at least 102° F., or alternatively at least 105° F.

Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician.

Suitable dosage formulations and methods of administering the agents can be readily determined by those of skill in the art. For example, the compositions are administered at about 0.01 mg/kg to about 200 mg/kg, alternatively at about 0.1 mg/kg to about 100 mg/kg, or alternatively at about 0.5 mg/kg to about 50 mg/kg. When the compounds described herein are co-administered with another agent (e.g., as sensitizing agents) or therapy, the effective amount may be less than when the agent is used alone.

The pharmaceutical compositions can be administered orally, intranasally, ocularly, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds.

More particularly, the composition of the invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active composition at sites of disease. Desirable blood levels of the agent may be maintained by a continuous infusion to provide a therapeutic amount of the active ingredient within disease tissue or at the site of disease or tumor by multiple administrations.

Transdermal delivery systems manufactured as an adhesive disc or patch which slowly releases the compositions described herein for percutaneous absorption can be used. To this end, permeation enhancers can be used to facilitate transdermal penetration of the therapeutic agent. Suitable transdermal patches are described in, for example, U.S. Pat. Nos. 5,407,713, 5,352,456, 5,332,213, 5,336,168, 5,290,561, 5,254,346, 5,164,189, 5,163,899, 5,088,977, 5,087,240, 5,008,110, and 4,921,475.

Screening Assays

This invention also provides screening assays to identify potential therapeutic agents of known and new compounds and combinations.

In one aspect, the assay requires contacting a first sample comprising suitable cells or tissue ("control sample") with an effective amount of a composition of this invention and contacting a second sample of the suitable cells or tissue ("test sample") with the agent to be assayed. The inhibition of growth of the first and second cell samples are determined. If the inhibition of growth of the second sample is substantially the same or greater than the first sample, then the agent is a potential drug for therapy. In one aspect, substantially the same or greater inhibition of growth of the cells is a difference of less than about 1%, or alternatively less than about 5% or alternatively less than about 10%, or alternatively greater than about 10%, or alternatively greater than about 20%, or alternatively greater than about 50%, or alternatively greater than about 90%. The contacting can be in vitro or in vivo. Means for determining the inhibition of growth of the cells are well know in the art and examples of such are disclosed herein, as Experiment #3 and #4. In a further aspect, the test agent is contacted with a third sample of cells or tissue comprising normal counterpart cells or tissue to the control and test samples and selecting agents that treat the second sample of cells or tissue but does not adversely effect the third sample. For the purpose of the assays described herein, a suitable cell or tissue is one involved in hyperproliferative disorders such as cancer or other diseases as described herein. Examples of such include, but are not limited to cancer cell or tissue obtained by biopsy, blood, breast cells, colon cells, liver cells, or synovial fluid. In one aspect, the samples comprise a primary central nervous system (CNS) tumor cell (gliomas, menengiomas, pituitary adenomas), a CNS cancer cell metastasis from a systemic cancer, lung cancer cell, prostate cancer cell, breast cancer cell, hematopoietic cancer cell or ovarian cancer cell.

Efficacy of the test composition is determined using methods known in the art which include, but are not limited to cell viability assays or apoptosis evaluation.

In yet a further aspect, the assay requires at least two cell types, the first being a suitable control cell.

The assays also are useful to predict whether a subject will be suitably treated by this invention by delivering a composition to a sample containing the cell to be treated and assaying for treatment which will vary with the pathology. In one aspect, the cell or tissue is obtained from the subject or patient by biopsy. Applicants provide kits for determining whether a pathological cell or a patient will be suitably treated by this therapy by providing at least one composition of this invention and instructions for use.

In another embodiment, a third target cell is used as a positive control because it receives an effective amount of a composition which have been shown to be potent.

The test cells can be grown in small multi-well plates and is used to detect the biological activity of test compounds. For the purposes of this invention, the successful candidate drug will block the growth or kill the pathogen but leave the control cell type unharmed.

Compounds, agents and combinations thereof, identified by this method are further provided herein.

The following examples are intended to illustrate, but not limit, the invention.

EXPERIMENTALS

Experiment #1

In vitro Efficacy

Current brain tumors are treated with intravenous or oral chemotherapy. Because the blood brain barrier prevents adequate delivery of conventional chemotherapy via these two routes, brain cancer is still largely untreatable. POH is delivered via nasal inhalation to the brain tumor. It has been demonstrated to be safely tolerated in patients, and to induce radiographic reduction in tumor size in patients with malignant gliomas. The mechanism of delivery is felt to be via the olfactory tract and systemically via the nasal vasculature.

The mechanism of POH action is thought to be via suppression of small G proteins synthesis, including Ras. In addition to malignant gliomas, POH has been demonstrated to be effective against a number of systemic malignancies including breast, lung, pancreatic, melanomas. It is currently administered via a nasal inhaler four times daily, and has been found to be well tolerated, with minimal side effects.

Figure 2:
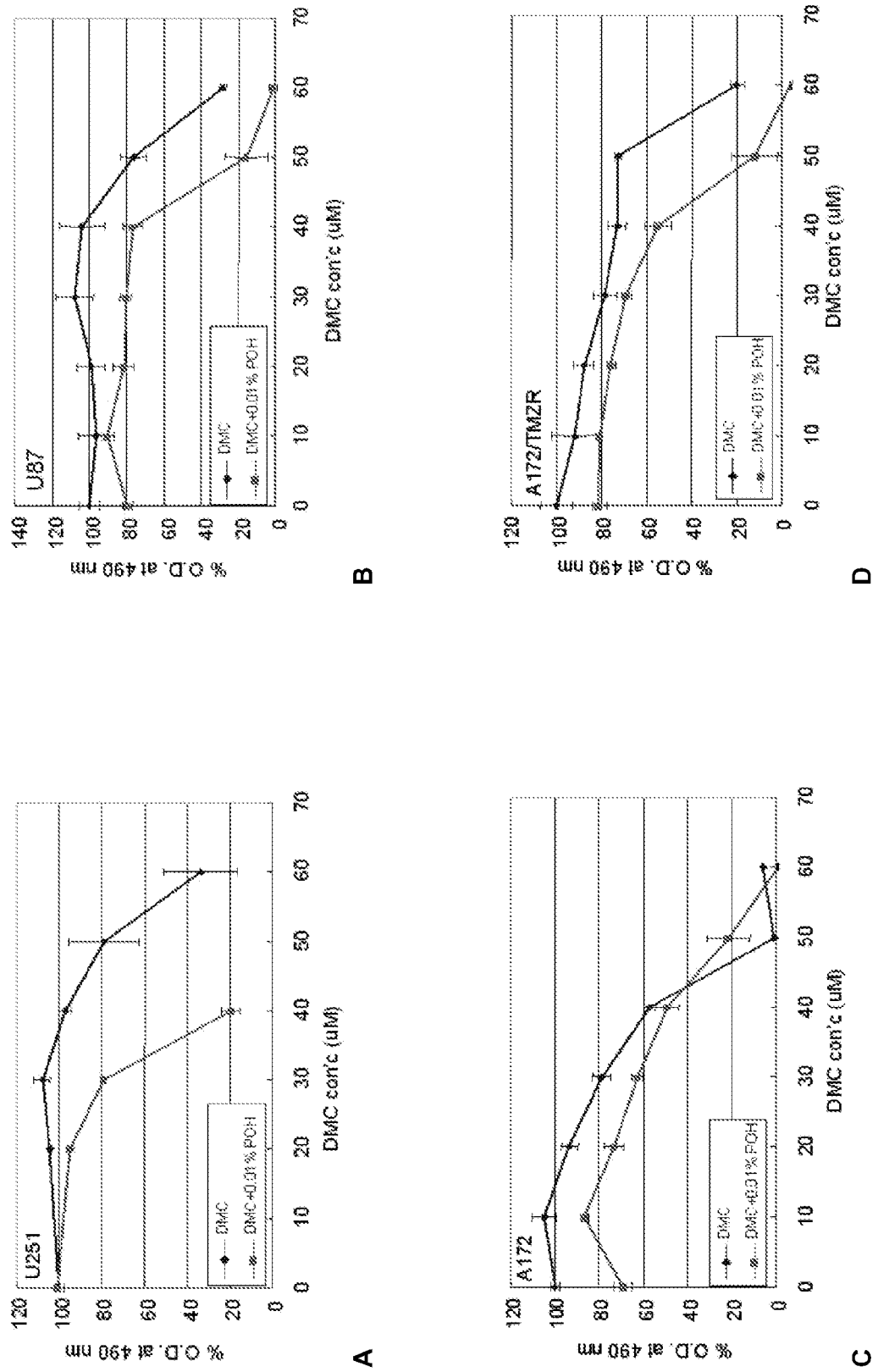
FIG. 2, Panels A through D, show a composition comprising POH and dimethyl-celecoxib induces greater cytoxicity in glioma cells than POH or dimethyl-celecoxib alone.

POH has never been used in combination treatment. Applicants have determined that POH may be used in combination with conventional chemotherapeutic agents such as temozolomide (TMZ; FIG. 1), or with more experimental agents (FIG. 2; i.e. dimethyl-celecoxib) to induce greater cytotoxicity in glioma cells than either drug alone. FIGS. 1A and 1C demonstrate that TMZ in combination with 0.01% POH has at least an additive effect in MTT cytotoxicity assays. This effect was less pronounced for U-87 glioma cells (FIG. 1B) and for A-172 TMZ resistant cells (FIG. 1D). This combination effect was even more pronounced when POH was combined with DMC. FIG. 2A-C demonstrates at least an additive effect for U-251, U-87, and A-172 cell lines. In combination with DMC, POH and DMC was even effective for A-172 TMZ resistant cells. U-251 is available from NCI-Frederick and is a CNS human glioblastoma cell line. See dtp.nci.nih.gov/docs/misc/common_files/cell_list.html, last accessed on Feb. 5, 2009. It also may be obtained from the ATCC.

Intranasal delivery provides a practical, noninvasive method for delivering therapeutic agents to the brain because of the unique anatomic connection provided by the olfactory and trigeminal nerves. These nerves connect the nasal mucosa and the CNS, allowing them to detect odors and other chemical stimuli. Intranasally administered drugs reach the parenchymal tissues of the brain and spinal cord and/or cerebrospinal fluid (CSF) within minutes using an extracellular route through perineural channels. In addition to bypassing the BBB, the advantages of intranasal delivery include rapid delivery to the CNS, avoidance of hepatic first-pass drug metabolism, and elimination of the need for systemic delivery, thereby reducing unwanted systemic side effects. Intranasal delivery also provides painless and convenient self administration by patients, features that encourage its use for delivering therapeutic agents into the CNS.

Experiment #2

Cell Culture

Human malignant gliomas U-87 and A-172 cells, can be obtained from the American Type Culture Collection (ATCC). Explanted specimen (GBM-1) can be obtained from a patient with glioblastoma multiforme using standard surgical procedures. Cells are grown as monolayers in 25 cm$^2$ tissue culture flasks in Dulbecco's modified Eagle medium supplemented with 0.2 mM non-essential amino acids, 10% fetal calf serum, penicillin (100 U/ml), streptomycin (100 μm/ml) and amphotericin B (fungizone, 2.5 mg/ml). For subcultures, cells are washed with phosphate-buffered saline (PBS, pH 7.2), detached by short exposure to trypsin and suspended in culture medium.

Experiment #3

Cell Viability Assay

Cells (10$^4$/ml) are cultivated in 96-well tissue culture plates for 24 h at 37° C., 5% $CO_2$. Cultures are then treated with DMEM or different concentrations of the composition (Sigma, St. Louis, Mo., USA). After 48 h, cells are treated with MTT (5 mg/ml), incubated for at least 4 h in the dark, and the formazan crystals are subsequently solubilized in 200 μl DMSO. The extension of reduction of MTT can be quantified by 570 nm absorbance measurement with a 630 nm reference filter.

Experiment #4

Apoptosis Evaluation

Apoptosis can be evaluated by cell morphology and cell cycle analysis. For morphology analysis, cells are grown in 25 cm$^2$ flasks, treated with medium or different concentrations of the composition before achieving confluence, then observed by optical microscopy for the next 48 h. For cell cycle analysis, cells (2×10$^5$/well) are plated in 24-well tissue culture plates, left to rest for 24 h, then treated with medium or different concentrations of the active agent and incubated for another 24 h. Cells are harvested, suspended and incubated for 1 h in a 300 μl/sample of hypotonic fluorescence solution (50 μg/ml propidium iodide (PI) and 0.1% Triton X-100 in 0.1% Na citrate buffer) at 4° C. for 1 h in the dark. DNA content is measured in the FL2 H channel using a fluorescent activated cell sorter scan flow cytometer (FACS Calibur; Becton-Dickinson, San Jose, Calif.). Data acquisition and analysis are controlled by CellQuest software version 3.1f. Events on 'sub-G1-peak' containing subdiploid DNA population were considered apoptotic.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains. Several aspects of the invention are listed below.

What is claimed:

1. A composition for administration by one or more of inhalation, intranasally or ocularly, comprising:
   a therapeutic agent;
   from about 0.0001% to about 0.01% (v/v) of perillyl alcohol, perillaldehyde or a carboxylic acid ester of perillyl alcohol;
   at least about 1.3% glycerol (v/v); and
   at least about 1.3% ethanol, (v/v),
   wherein the components equal 100% (v/v) of the composition.

2. A composition for administration by one or more of inhalation, intranasally or ocularly, consisting essentially of:
   a therapeutic agent;
   from about 0.0001% to about 0.01% (v/v) of perillyl alcohol, perillaldehyde or a carboxylic acid ester of perillyl alcohol;
   at least about 1.3% glycerol (v/v); and
   at least about 1.3% ethanol, (v/v),
   wherein the components equal 100% (v/v) of the composition.

3. The composition of claim 1, wherein the composition comprises perillyl alcohol.

4. The composition of claim 1 or 2, wherein the therapeutic agent is a chemotherapeutic agent or a therapeutic antibody.

5. The composition of claim 1 or 2, wherein the therapeutic agent is temozolomide or dimethylcelecoxib.

6. The composition of claim 1 or 2, formulated for pediatric administration.

7. The composition of claim 1 or 2, wherein the therapeutic agent treats a neurological disorder or a cancer affecting the central nervous system.

8. A kit comprising the composition of claim 1 or 2, a device for administering the composition by inhalation and instruction for use of the device.

9. The composition of claim 1 or 2, wherein the perillyl alcohol, perillaldehyde or a carboxylic acid ester of perillyl alcohol is present in an amount from about 0.001% to about 0.01% (v/v).

10. The composition of claim 1 or 2, wherein the perillyl alcohol, perillaldehyde or a carboxylic acid ester of perillyl alcohol is present in an amount of about 0.01% (v/v).

* * * * *